United States Patent
Savard (10) Patent No.: US 9,182,281 B1
(45) Date of Patent: Nov. 10, 2015

(54) ROBUST TERAHERTZ SPECTROMETER CONFIGURATION AGAINST SCANNER HEADS MISALIGNMENT

(71) Applicant: Stephane Savard, Vancouver (CA)

(72) Inventor: Stephane Savard, Vancouver (CA)

(73) Assignee: Honeywell ASCA Inc., Mississauga (CA)

(*) Notice: Subject to any disclaimer, the term of this patent is extended or adjusted under 35 U.S.C. 154(b) by 61 days.

(21) Appl. No.: 14/291,629

(22) Filed: May 30, 2014

(51) Int. Cl.
*G01J 3/00* (2006.01)
*G01J 3/10* (2006.01)
*G01J 3/42* (2006.01)
*G01J 3/02* (2006.01)

(52) U.S. Cl.
CPC ............... *G01J 3/108* (2013.01); *G01J 3/021* (2013.01); *G01J 3/42* (2013.01)

(58) Field of Classification Search
CPC ............... G01J 3/02; G01J 3/28; G01J 3/42; G01N 21/31; G01N 21/552
USPC ................................................. 356/300–445
See application file for complete search history.

(56) References Cited

U.S. PATENT DOCUMENTS

| 6,252,667 B1* | 6/2001 | Hill ............... G03F 7/70716 |
| | | 356/487 |
| 7,609,366 B2 | 10/2009 | MacHattie |
| 7,688,447 B2 | 3/2010 | Shakespeare |
| 8,378,304 B2 | 2/2013 | Mousavi |
| 8,457,915 B2 | 6/2013 | White |
| 8,638,443 B2 | 1/2014 | Haran |

OTHER PUBLICATIONS

International Search Report, Jul. 27, 2015 for PCT/CA2015/00303.

* cited by examiner

*Primary Examiner* — Abdullahi Nur
(74) *Attorney, Agent, or Firm* — Cascio Schmoyer & Zervas (57) ABSTRACT

Robust terahertz time-domain spectrometer has a reflective surface arrangement that renders the sensor insensitive to x or y displacement. The apparatus includes: (a) first scanner head; (b) a first reflective surface; (c) emitter; (d) beam splitter to yield reference radiation pulses and sample radiation pulses; (e) first reflector to reflect sample radiation pulses that have been transmitted through the sample to generate reflected sample radiation pulses that are directed towards a web; (f) second reflector that reflects the reference radiation pulses to generate reflected reference radiation pulses that are directed towards the beam splitter which in turn transmits a portion of the reflected references radiation pulses towards the web; and (g) a detector that receives (i) the reflected sample radiation pulses that have interacted with the sample a plurality of times and (ii) reflected reference radiation pulses that have interacted with the sample a plurality of times.

20 Claims, 5 Drawing Sheets

ROBUST TERAHERTZ SPECTROMETER CONFIGURATION AGAINST SCANNER HEADS MISALIGNMENT

FIELD OF THE INVENTION

The present invention generally relates to time-domain spectrometers that enable the sample pulses' phase and amplitude to be tracked and corrected by means of reference pulses thereby significantly increasing the measurement precision of the spectrometers and more particularly to techniques to minimized the effects of scanner head misalignment especially when applied to dual head terahertz spectrometers.

BACKGROUND OF THE INVENTION

Time-domain systems are important analytical tools for measuring properties of an object. Recently, terahertz systems known as terahertz time-domain spectrometers (THz-TDS) have been developed. These systems often use visible to near-infrared laser pulses each lasting only 10 to several hundred femtoseconds to electromagnetic pulses ("T-rays") that each last for about a picosecond. T-rays can be transmitted through various objects, using an imaging system of lenses and mirrors to focus or collimate the T-rays. As the T-rays pass through the object under test, they are typically distorted. These changes in the T-ray signals can be analyzed to determine properties of the object. Materials can be characterized by measuring the amounts of distortion—from absorption, dispersion and reflection—of the T-rays passing through to a detector. A digital signal processing system takes the digitized data from the THz detector and analyzes the data in either the spectral or temporal domain.

Because many compounds change T-rays in characteristic ways (e.g., absorption or dispersion), molecules and chemical compounds show strong absorption lines that can serve as "fingerprints" of the molecules. T-ray spectroscopy can distinguish between different chemical compositions inside a material even when the object looks uniform in visible light. A terahertz sensor for instance can be employed to measure caliper, moisture, and basis weight of paper whose thickness is similar to the wavelengths of T-Rays.

The precision of amplitude and phase measurements in time-domain (terahertz) spectroscopy (THz-TDS) is often limited by noise in the system. It has been demonstrated that the dominant types of noise present in THz-TDS are often time base and amplitude jitter characterized by pulses traveling through the same material (or air) which reach the detector at slightly different times and with slightly different amplitudes due to fluctuations in environmental parameters (e.g., temperature fluctuations or vibrations) or hardware errors (e.g., encoder errors in the delay line). In some specific THz-TDS systems, jitter makes a significant contribution to the noise and therefore limits the measurement precision of the system. In other THz-TDS systems, it is the multiplicative noise (i.e., amplitude noise), which comes primarily from the laser that is the main source of imprecision.

U.S. Pat. No. 8,378,304 to Mousavi et al. discloses an apparatus for implementation of time-domain spectroscopy that creates a continuous set of reference pulses whereby a sample pulses' phase and amplitude can be tracked and corrected. The apparatus can be readily adopted into existing time-domain spectrometers where both amplitude and phase are of interest. A feature of the apparatus is that when it is employed in a THz-TDS, the effect of jitter can be significantly reduced.

U.S. Pat. No. 8,638,443 to Haran and Savard discloses a method, for compensating for errors in spectrometers, that includes measuring at least a portion of a path length for a signal traveling through the spectrometer during a measuring scan of a material. The detector signal corresponding to the measurement scanner is generated. Compensation for errors in the detector and signal is provided based on the measurement path length.

Typically, on-line spectrometer sensor devices are operated to periodically traverse, or "scan," traveling webs of sheet material during manufacture. Scanning usually is done in the cross direction, i.e., in the direction perpendicular to the direction of sheet travel. These sensors typically employ single or double sided packages which traverse the width of the sheet, guided on rail systems affixed to stiff beam structures. The accuracy of the sensor system is related to the relative x, y, and z displacement alignment between upper and lower sensor halves. The scanner heads can become misaligned up to a few millimeters or more between forward and backward scanning directions. Even small displacements can adversely affect the detected THz signal.

SUMMARY OF THE INVENTION

The present invention is directed to a robust terahertz spectrometer that incorporates reflective surface arrangement that renders the sensor insensitive to x or y displacement especially when the spectrometer has dual scanner heads.

In one aspect, the invention is directed to a time-domain spectroscopy apparatus, that has a continuous reference for measuring at least one property of a sample that is a continuous web having a first side and a second side which travels in a downstream direction, that includes:

(a) a first scanner head disposed adjacent to the first side of the web, the first scanner head having a first operative surface facing the first side of the web;

(b) a first reflective surface facing the second side of the web;

(c) an emitter positioned in the first scanner head that generates pulses of radiation;

(d) means for splitting the pulses of radiation to yield reference radiation pulses and sample radiation pulses wherein the sample radiation pulses are directed to the first side of the web;

(e) a first reflector positioned in the first scanner head to reflect sample radiation pulses that have been transmitted through the sample to generate reflected sample radiation pulses that are directed towards the web;

(f) a second reflector positioned in the first scanner head that reflects the reference radiation pulses to generate reflected reference radiation pulses that are directed towards the means for splitting the pulses of radiation which transmits a portion of the reflected references radiation pulses towards the web; and (g) a detector positioned in the first scanner head to receive (i) the reflected sample radiation pulses that have interacted with the sample a plurality of times before being detected and (ii) reflected reference radiation pulses that have interacted with the sample a plurality of times before being detected.

In one embodiment of the apparatus that has dual scanner heads, a second scanner head is disposed adjacent to the second side of the web. The second scanning head has a second operative surface facing the second side of the web and includes the first reflective surface. The first and second scanner heads move in a synchronized fashion along a cross direction. In another embodiment of the apparatus, the first reflective surface is formed on a metallic roll or on an elongated beam, that is positioned parallel to movement of the first scanner head.

In a further aspect, the invention is directed to a method of improving the precision of a time-domain spectroscopy apparatus that includes an emitter, positioned in a first scanner head that generates pulses of radiation, and a detector, positioned in the first mounting head that receives pulses of radiation that interacts with a sample that is a continuous web, the method including the steps of:

positioning a first reflective surface;
positioning a sample reflector in the first scanner head;
positioning a reference reflector in the first scanner head;
positioning a planar beam splitter along an optical path between the emitter and the detector to branch pulses of radiation from the emitter into sample radiation pulses and reference radiation pulses wherein the planar beam splitter and the first reflective surface are parallel and define a portion of the measurement gap through which the continuous web travels; and
directing the pulses of radiation from the emitter at the planar beam splitter at an incident angle between 0 and 90 degrees such that the sample radiation pulses interact with the sample a plurality of times along a first optical path between the sample reflector and the detector and such that the reference radiation pulses interact with the sample a plurality of times along a second optical path between the reference reflector and the detector.

With the present invention, by orienting the incident beam, such as THz radiation, from the emitter at a sufficiently small angle relative to the beam splitter, the displacement at the converging lens at the detector will be small even with misalignment. In addition, the z displacement that is between the scanner heads can be corrected by measurement of a reference beam. Finally, with the novel configuration both the sample beam and the reference beam goes through the sheet a plurality of times thereby improving sensor precision.

DESCRIPTION OF PREFERRED EMBODIMENTS

The present invention is directed to techniques for enhancing the precision of time-domain spectroscopy systems, which can be implemented by modifying standard time-domain spectrometers. While the invention will be described in relationship with a terahertz time-domain spectrometer, it is understood that the invention improves the precision of any time-domain spectrometer wherein pulses of radiation are applied to a sample and the time resolved characteristics of transmitted pulses that emerge from the sample are analyzed.

Figure 1:
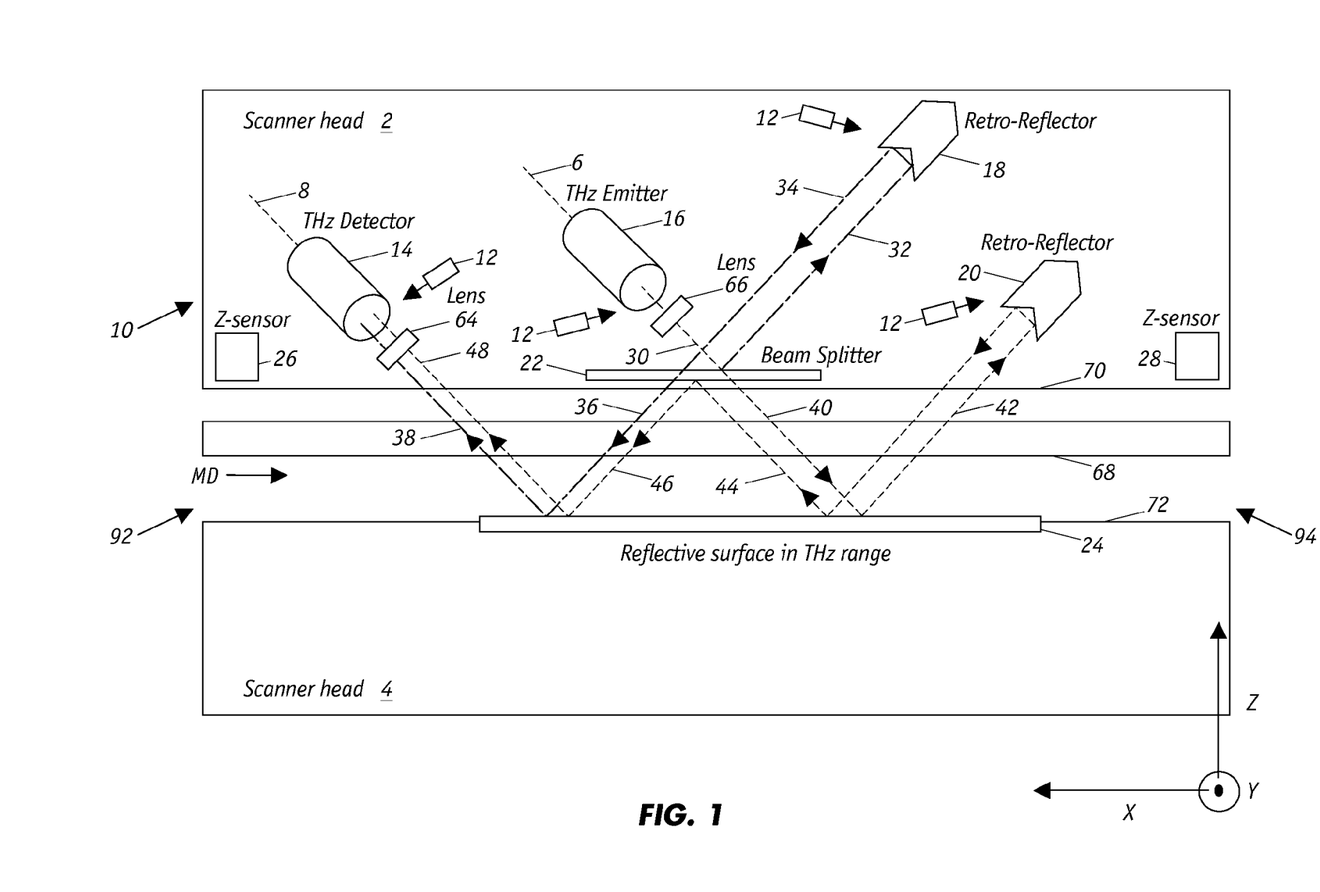
FIGS. 1 and 3 depict dual scanner head devices for generating continuous referencing in time-domain spectroscopy.

FIG. 1 illustrates one embodiment of the continuous real time referencing generating device 10 that include scanner sensor heads 2 and 4. The upper scanner head 2 houses emitter 16, retro-reflectors or mirrors 18, 20, detector 14 and beam splitter 22. The lower head 4 includes a reflective surface 24. The operative surfaces 70 and 72 on the upper and lower scanner heads 2 and 4, respectively, define a measurement gap through which a web of material 68, such as paper, moves in the machine direction (MD). Lateral openings 92 and 94 of the measurement gap allow the scanner to move in a perpendicular cross direction (CD) as the paper travels in the MD. Openings 92 and 94 serve as the web entry and web exit, respectively. Movement of the dual scanner heads 2, 4 is synchronized with respect to speed and direction so that they are aligned with each other.

The planar beam splitter 22 is parallel with the planar specular reflective surface 24 which can consist of a mirror. For terahertz radiation, a preferred beam splitter comprises a thick piece of high resistivity (>10,000 O-cm) silicon slab. The thickness of the beam splitter is selected to be large enough so that reflections from the back surface thereof lie outside the measurement window. If a thinner beam splitter is used, the pulse shape will look different since multiple reflections from the backside are included in the window. In principal either configuration can be employed with the present invention. A thicker beam splitter is preferred because it is less prone to vibrate. The high resistivity silicon slab is particularly suited for use as a beam splitter as it has a high refractive index with acceptable absorption in terahertz frequencies. Alternatively, sapphire or polyethylene could be used as the beam splitter although they have higher absorption than that of silicon. For terahertz spectrometers, the emitter and detector can be, for example, photoconductive antennae.

Emitter 16 and associated focusing lens 66 generate incident light 30 that is incident on the beam splitter at an incident angle that ranges from greater than 0 to 90 degrees and preferably from 15 to 75 degrees. Retro-reflector 18 is oriented to reflect light that is branched from beam splitter 22, retro-reflector 20 is oriented to reflect light that is reflected from reflective surface 24, and detector 14 and associated converging lens 64 is oriented to capture light reflected from reflective surface 24. Sources of dry air 12 are positioned to prevent debris from interfering with detector 14, emitter 16 and retro-reflectors 18 and 20. Dry air can also be used to purge debris along the optical paths. Tilting between the two scanner heads could introduce errors to the measurement. Low-resolution z-sensors 26 and 28 can be employed to continuously account for this displacement by measuring the z gap distance between the scanner heads.

In operation, laser pulses 6 and 8 are directed to emitter 16 and detector 14, respectively. Initially, a terahertz radiation pulse that is generated by emitter 16 is incident on beam splitter 22 at a small incident angle resulting in two pulses traveling in perpendicular directions. Pulse 40 is transmitted through sample 68 whereas the reflected pulse 32 is used to track the fluctuations in time and amplitude. Since the two pulses are generated at the same time and position, their phases and amplitudes correlate very strongly and this correlation is used to correct measurement errors. A pulsed laser source (such as a femtosecond (fs) laser) can be employed to generate laser pulses 6 and 8. Typically, the fs laser emits a beam of optical pulses and a beam splitter splits the optical pulses into two beams, a reflected beam and a transmitted beam. The transmitted beam comprising laser pulses 6 is directed to the emitter 16 whereas the reflected beam comprising laser pulses 8 is delayed a specified amount of time before being directed to detector 14.

Transmitted light 42 is reflected by reflective surface 24 into retro-reflector 20 and the returned light 44 is reflected by reflective surface 24 towards beam splitter 22. Light 44 is partially reflected by beam splitter 22 towards reflective surface 24 and partially transmitted into lens 66 and emitter 16.

The reflected light 46 is thereafter reflected by reflective surface 24 to generated sample light 38 that is collected by converging lens 64 into detector 14. Pulses of light 40 from emitter 16 travel through and interact with different parts of the sample web 68. In this configuration, the sample light passes through web 68 six times as the light propagates through the measurement gap.

With respect to reflected light 32 which is directed toward retro-reflector 18, the returned light 34 is partially reflected by beam splitter into lens 66 and emitter 16 and the remaining portion consisting of light 36 is transmitted through beam splitter 22 towards reflective surface 24. Reference light 48 is collected by lens 64 into detector 14. The reference light passes through web 68 twice as the light propagates through the measurement gap. It is preferred that the positions of detector 14, emitter 16, and retro-reflectors 18 and 20 be aligned so that the sample and reference lights propagate along the machine direction.

The tolerance for this design in the x-y plane depends on the mirror dimensions and could be in the centimeter range, for instance, which is large enough for industrial applications, such as, for monitoring paper in a paper making machine. The tolerance it is difficult to assess in the z direction (the gap) because the tolerance depends on the two scanner heads' mechanical spacing (gap), the optical path and components used. Thus if the system as a 5 cm diameter beam splitter (22), beam (30) width of 3 cm incident at 45 deg, retro-reflector (20) and lens (64) both having a 5 cm diameter and heads gap being 2.5 cm, then the system depicted in FIG. 2 would be robust against ±300 micron variations which are typical z variations encountered in industrial scanners.

Figure 2:
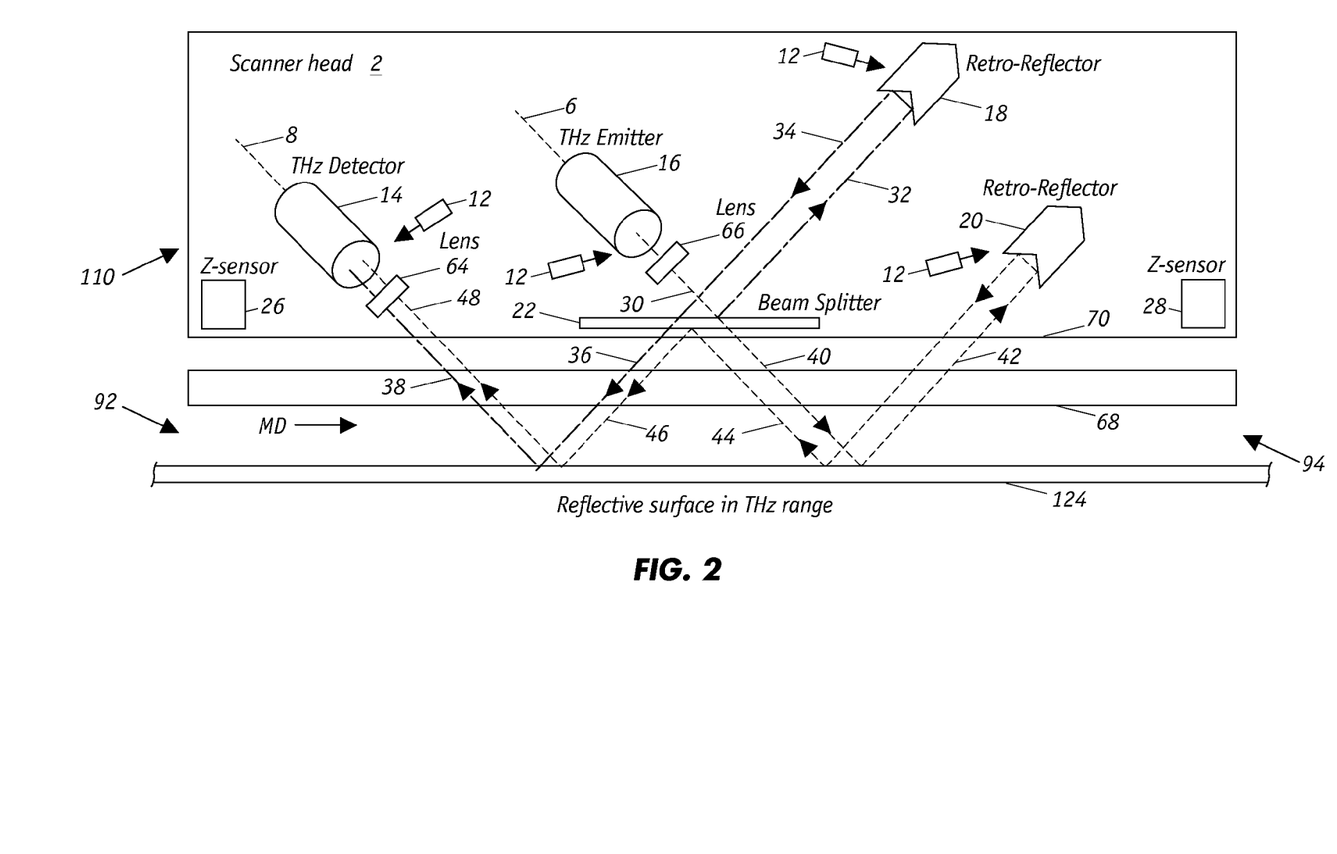
FIGS. 2 and 4 depict devices with for generating continuous referencing in time-domain spectroscopy wherein the lower reflective surface is formed on a metallic roll or beam.

FIG. 2 illustrates another embodiment of the continuous real time referencing generating wherein like reference numbers refer to the same features described in FIG. 1. Spectrometer 110 employs a reflective surface 124 instead of the lower scanner head 4 (FIG. 1). As shown in FIG. 2, the reflective surface 124 can be formed on a metallic roll, elongated beam member or any suitable substrate that presents a planar specular reflecting surface.

Figure 3:
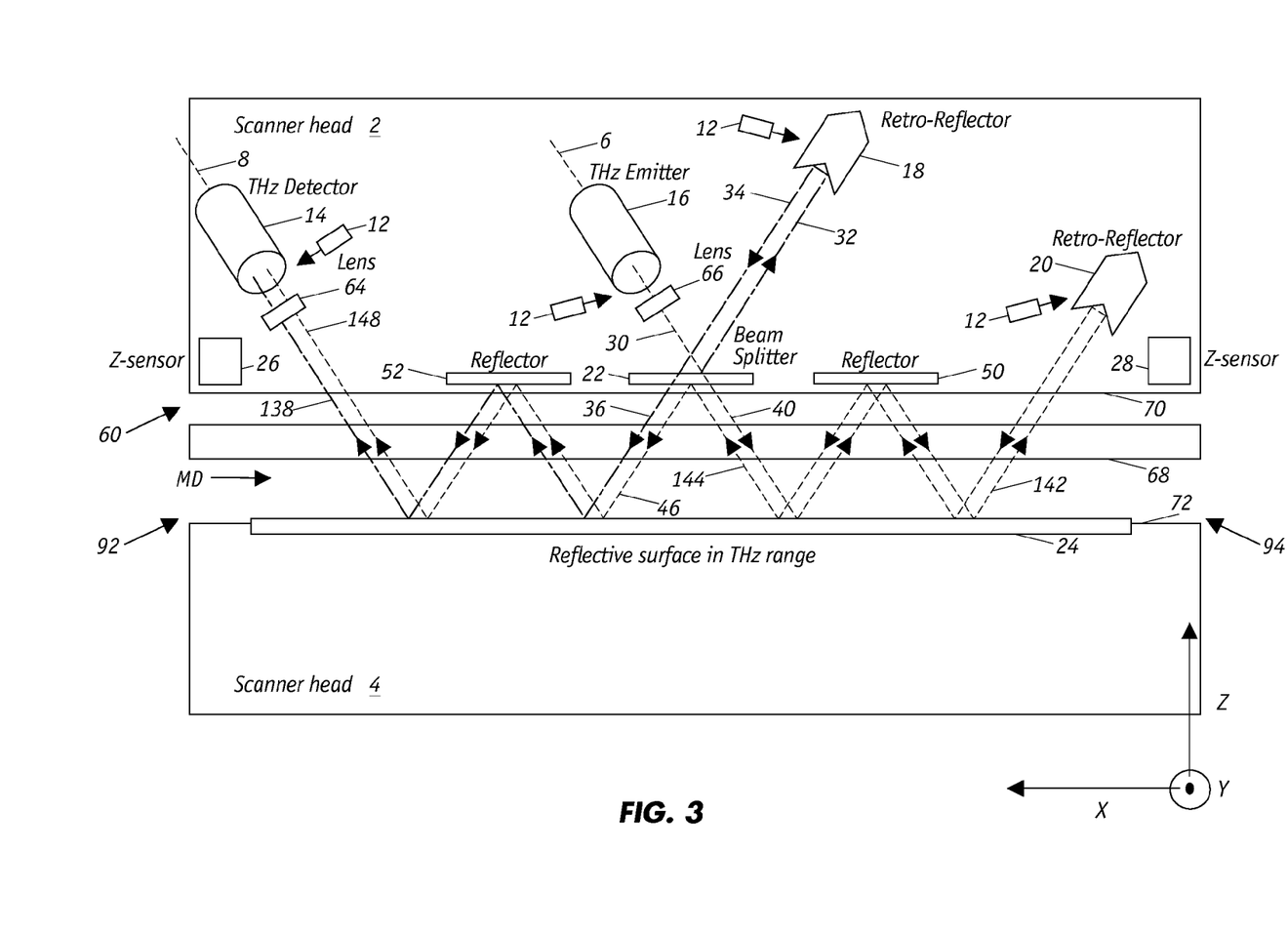

FIG. 3 illustrates another embodiment of the continuous real time referencing generating device 60 that include scanner sensor heads 2 and 4. The upper scanner head 2 houses emitter 16, retro-reflectors or mirrors 18, 20, detector 14 and beam splitter 22. The lower head 4 includes a reflective surface 24. The operative surfaces 70 and 72 of the upper and lower scanner heads 2 and 4, respectively, define a measurement gap through which a web of material 68, such as paper, moves in the MD. Lateral openings 92 and 94 of the measurement gap. Movement of the dual scanner heads 2, 4 is synchronized with respect to speed and direction so that they are aligned with each other.

The planar beam splitter 22 is parallel with the planar specular reflective surface 24 which can consist of a mirror. Specular reflectors 50 and 52 are positioned along the downstream and upstream position relative to beam splitter 22. Emitter 16 and associated focusing lens 66 generate incident light 30 that is incident on the beam splitter at an incident angle that ranges from greater than zero to 90 degrees and preferably from 15 to 75 degrees. Retro-reflector 18 is oriented to reflect light branched from beam splitter 22, retro-reflector 20 is oriented to reflect light that is reflected from reflective surface 24, and detector 14 is oriented to capture light that is reflected from reflective surface 24. Sources of purging dry air 12 are strategically located in the spectrometer. Tilting between the two scanner heads is accounted for with low-resolution z-sensors 26 and 28.

In operation, laser pulses 6 and 8 are directed to emitter 16 and detector 14, respectively. Initially, a terahertz radiation pulse is generated by emitter 16 is incident on beam splitter 22 at a small angle resulting in two pulses traveling in perpendicular directions. Pulse 40 is transmitted through sample web 68 whereas the reflected pulse 32 is used to track the fluctuations in time and amplitude. Since the two pulses are generated at the same time and position, their phases and amplitudes correlate very strongly and this correlation is used to correct measurement errors.

Transmitted light 142 is reflected by reflective surface 24 and reflector 50 as the light travels into retro-reflector 20. Similarly, returned light 144 is reflected by reflective surface 24 and reflector as the light travels towards beam splitter 22. Light 144 is partially reflected by beam splitter 22 towards reflective surface 24 and partially transmitted into lens 66 and emitter 16. The reflected light 46 is thereafter reflected by reflective surface 24 to generated sample light 138 that is focused by lens 64 into detector 14. Pulses of light 40 from emitter 16 travel through and interact with different parts of the sample web 68. In this configuration, the sample light passes through web 68 eight times as the light propagates through the measurement gap.

With respect to reflected light 32 which is directed toward retro-reflector 18, the returned light 34 is partially reflected by beam splitter 22 into lens 66 and emitter 16 and the remaining portion consisting of light 36 is transmitted through beam splitter 22 towards reflective surface 24. Reference light 148 is focused by lens 64 into detector 14. The reference light, which is reflected by reflective surface 24 and reflector 52 passes through web 68 four times as the light propagates through the measurement gap. It is preferred that the positions of detector 14, emitter 16, and retro-reflectors 18 and 20 be aligned so that the sample and reference lights propagate along the machine direction.

Figure 4:
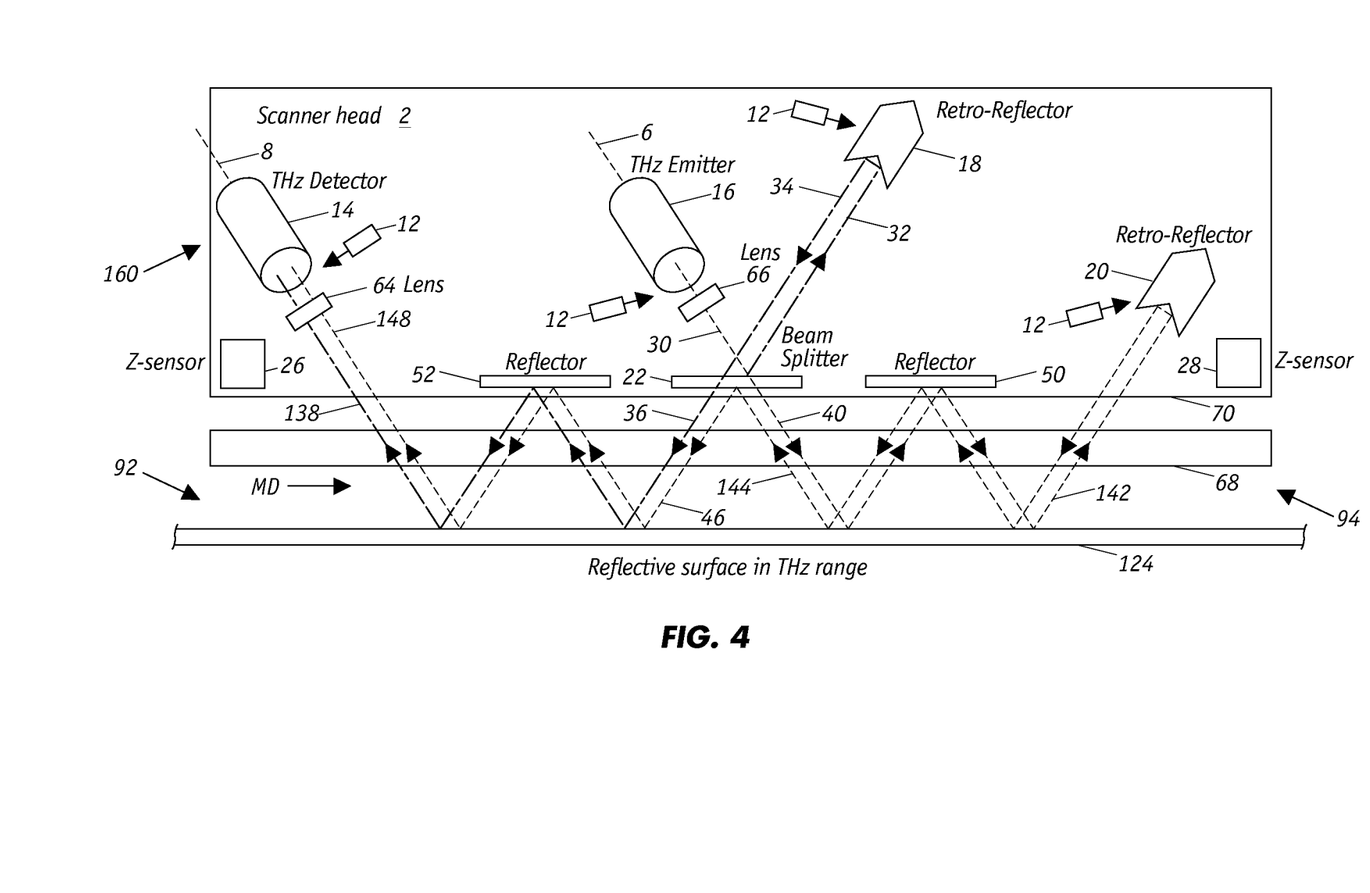

FIG. 4 illustrates another embodiment of the continuous real time referencing generating wherein like reference numbers refer to the same features described in FIG. 3. Spectrometer 160 employs a reflective surface 124 instead of a lower scanner head 4 (FIG. 3). As shown in FIG. 4, the reflective surface 124 can be formed on a metallic roll, elongated beam member or any suitable substrate that presents a planar specular reflecting surface.

Figure 5:
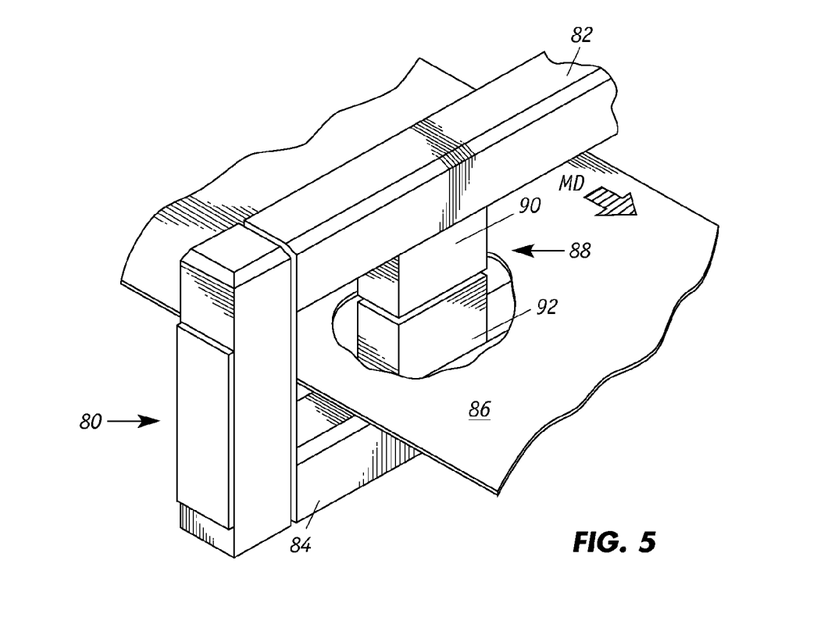
FIGS. 5 and 6 show sheetmaking systems implementing the robust spectrometer configurations.

FIG. 5 illustrates a particular implementation of the robust terahertz spectrometers that have dual scanner heads as depicted in FIGS. 1 and 3. In particular, the emitter, beam splitter, detector, retro-reflectors, and reflective surface are housed in a dual head scanner 88 of scanner system 80 which can be employed to measure properties in paper or materials. Upper scanner head 90 moves repeatedly back and forth in the CD across the width of the moving sheet 86, which moves in the MD, so that the characteristics of the entire sheet are measured. Scanner 88 is supported by two transverse beams 82, 84 on which are mounted upper and lower scanning heads 90, 92. The operative faces of the lower and upper scanner heads 90, 92 define a measurement window or cell that accommodates sheet 86. The lower scanner head 92 may include a sheet stabilization system such as an air-bearing stabilizer (not shown) to maintain the sheet on a consistent plane as it passes through the measurement cell. The movement of the dual scanner heads 90, 92, is synchronized with respect to speed and direction so that they are aligned with each other.

Figure 6:
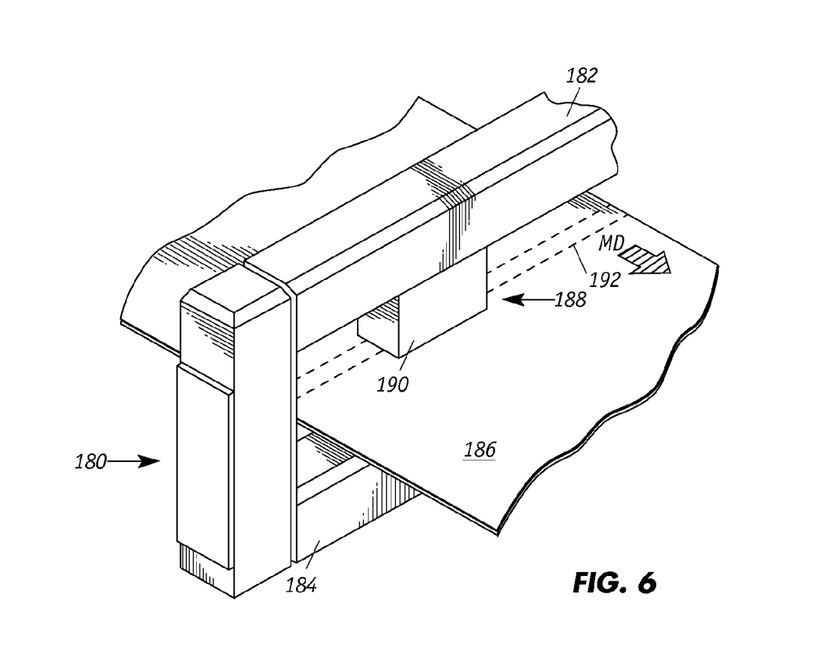

FIG. 6 illustrates a particular implementation of the robust terahertz spectrometers that employ a single scanner head as depicted in FIGS. 2 and 4. In particular, the emitter, beam splitter, detector and retro-reflectors, and reflective surface are housed in scanner 190 of scanner system 180. Scanner system 188 is supported by two transverse beams 182, 184 with upper scanning head 190 being mounted to traverse along the axis of beam 182. A reflective substrate 192 is positioned below scanner head 190 such that operative face of upper scanner head 190 and the reflective substrate 192 define a measurement gap that accommodates sheet 186. Upper scanner head 90 moves repeatedly back and forth in the CD across the width of the moving sheet 186. The reflective substrate 192 is stationary.

The present invention can be implemented in time-domain spectroscopy systems. Near THz or THz-TDS can be used in-situ to coincidentally obtain one or more parameters/properties of a sheet material including the water weight, physical thickness (caliper) and dry weight volume fraction. The sheet material can comprise paper or a plastic. From these parameters/properties in combination with one or more calibration parameters, caliper, basis weight and moisture content and other physical characteristics of the sheet material may be obtained.

An algorithm for using data entails conducting a calibration whereby reference measurements of pulses (36) and (40) is taken without any web product positioned between the scanner heads and the measurements are stored in memory. In operation, measurements of pulses (36) and (40) are taken repeatedly to extract product parameters. The product will induce a different shift in time and modify the shape or amplitude differently on both (36) and (40). In order to extract the product parameters, different transfer functions using Fresnel equations are applied on pulses (36) and (40) to reproduce the ones measured. Residuals are minimized to get accurate values of product composition.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A time-domain spectroscopy apparatus, that has a continuous reference for measuring at least one property of a sample that is a continuous web having a first side and a second side, which travels in a downstream direction, that comprises:
    (a) a first scanner head disposed adjacent to the first side of the web, the first scanner head having a first operative surface facing the first side of the web;
    (b) a first reflective surface facing the second side of the web;
    (c) an emitter positioned in the first scanner head that generates pulses of radiation;
    (d) means for splitting the pulses of radiation to yield reference radiation pulses and sample radiation pulses wherein the sample radiation pulses are directed to the first side of the web;
    (e) a first reflector positioned in the first scanner head to reflect sample radiation pulses that have been transmitted through the sample to generate reflected sample radiation pulses that are directed towards the web;
    (f) a second reflector positioned in the first scanner head that reflects the reference radiation pulses to generate reflected reference radiation pulses that are directed towards the means for splitting the pulses of radiation which transmits a portion of the reflected references radiation pulses towards the web; and
    (g) a detector positioned in the first scanner head to receive (i) the reflected sample radiation pulses that have interacted with the sample a plurality of times before being detected and (ii) reflected reference radiation pulses that have interacted with the sample a plurality of times before being detected.

2. The apparatus of claim 1 wherein the emitter generates an emitter signal that is incident on the means for splitting the pulses of radiation at an angle of incidence that is between 15 to 75 degrees.

3. The apparatus of claim 1 comprising a second scanner head disposed adjacent to the second side of the web, the second scanning head having a second operative surface facing the second side of the web, wherein the first operative surface and the second operative surface define a measurement gap through which the web travels, wherein the measurement gap has a web entry end and a web exit end that is downstream from the web entry end and wherein the second scanner head includes the first reflective surface.

4. The apparatus of claim 3 wherein the first scanner head and the second scanner head move in a synchronized fashion along a cross direction.

5. The apparatus of claim 3 comprising a sensor that measures the tilt between the first scanner head and the second scanner head.

6. The apparatus of claim 1 wherein the first reflective surface is formed on a metallic roll or on a beam.

7. The apparatus of claim 1 wherein the means for splitting the pulses of radiation comprises a beam splitter that is positioned in the first scanner head such that the beam splitter and reflective surface are parallel.

8. The apparatus of claim 7 wherein the emitter generates an emitter signal that is incident on the beam splitter surface at a first incident angle that is between 15 to 75 degrees.

9. The apparatus of claim 8 wherein the detector collects radiation pulses that have been reflected from the first reflective surface at an angle of reflection, wherein the first reflector directs radiation pulses toward the web at a second incident angle and wherein the second reflector directs radiation pulses toward the means for splitting the pulses of radiation at a third incident angle.

10. The apparatus of claim 8 wherein the angle of reflection, the first angle of incident, the second angle of incident and the third angle of incident are the same.

11. The apparatus of claim 1 wherein the means for splitting the pulses of radiation comprising a planar beam splitter.

12. The apparatus of claim 1 wherein the first scanner head comprises a second reflective surface facing the first reflective surface such that radiation pulses are reflected between the first and second reflective surfaces a plurality of times as radiation pulses propagate through the web in a direction that is parallel to the machine direction and the first scanner head comprises a third reflective surface facing the first reflective surface such that radiation pulses are reflected between the first and third reflective surfaces a plurality of times as radiation pulses propagate through the web in a direction that is parallel to the machine direction.

13. The apparatus of claim 1 wherein the emitter generates an emitter signal and the detector generates a detector signal based on the emitter signal.

14. The apparatus of claim 1 the first reflector comprises a mirror or a retro reflector and the second reflector comprises a mirror or a retro reflector.

15. The apparatus of claim 1 comprising:
    a laser source that generates pulses of radiation; and means for splitting the pulses of radiation from the laser source to yield first radiation pulses and second radiation pulses;

wherein the emitter generates terahertz frequency signal pulses when excited by the first radiation pulses from the laser source and wherein the detector receives terahertz frequency radiation that has interacted with the sample and that generates detection signals when excited by the second radiation pulses.

16. A method of improving the precision of a time-domain spectroscopy apparatus that includes an emitter, positioned in a first scanner head that generates pulses of radiation, and a detector, positioned in the first scanner head that receives pulses of radiation that interacts with a sample that is a continuous web, the method comprising the steps of:

positioning a first reflective surface;
positioning a sample reflector in the first scanner head;
positioning a reference reflector in the first scanner head;
positioning a planar beam splitter along an optical path between the emitter and the detector to branch pulses of radiation from the emitter into sample radiation pulses and reference radiation pulses wherein the planar beam splitter and the first reflective surface are parallel and define a portion of the measurement gap through which the continuous web travels; and directing the pulses of radiation from the emitter at the planar beam splitter at an incident angle of between 0 to 90 degrees such that the sample radiation pulses interact with the sample a plurality of times along a first optical path between the sample reflector and the detector and such that the reference radiation pulses interact with the sample a plurality of times along a second optical path between the reference reflector and the detector.

17. The method of claim 16 wherein the first reflective surface is positioned in a second scanner head, wherein the first and second scanner heads define a measurement gap through which the continuous web travels, and wherein the measurement gap has a web entry end and a web exit end that is downstream from the web entry end.

18. The method of claim 16 wherein the time-domain spectroscopy apparatus is insensitive to misalignment between the planar beam splitter and the first reflective surface.

19. The method of claim 16 comprising applying dry gas to purge debris away from the sample reflector, reference reflector, emitter and optical paths of the radiation.

20. The method of claim 16 wherein the emitter generates an emitter signal that is incident on the means for splitting the pulses of radiation at an angle of incidence that is between 15 to 75 degrees.

* * * * *